United States Patent [19]

McEachern

[11] Patent Number: 5,680,028
[45] Date of Patent: Oct. 21, 1997

[54] CHARGER FOR HAND-HELD RECHARGEABLE ELECTRIC APPARATUS WITH REDUCED MAGNETIC FIELD

[76] Inventor: Alexander McEachern, 6067 Rockridge Blvd., Oakland, Calif. 94618

[21] Appl. No.: 309,945

[22] Filed: Sep. 21, 1994

Related U.S. Application Data

[63] Continuation-in-part of Ser. No. 269,392, Jun. 30, 1994, abandoned.

[51] Int. Cl.$^6$ .................................................. H01M 10/46
[52] U.S. Cl. ........................................ 320/2; 336/DIG. 2
[58] Field of Search ...................... 320/2, 5; 336/DIG. 2

[56] References Cited

U.S. PATENT DOCUMENTS

| | | | |
|---|---|---|---|
| 2,415,688 | 2/1947 | Hall, Jr. . | |
| 2,483,815 | 10/1949 | Easton . | |
| 2,967,267 | 1/1961 | Steinman et al. . | |
| 3,277,358 | 10/1966 | Nicholl | 320/59 |
| 3,292,579 | 12/1966 | Buchanan . | |
| 3,329,880 | 7/1967 | Boyles | 320/2 |
| 3,418,552 | 12/1968 | Holmes | 320/2 |
| 3,549,990 | 12/1970 | Hochheiser . | |
| 3,641,336 | 2/1972 | Boin . | |
| 3,772,625 | 11/1973 | Raupach . | |
| 3,840,795 | 10/1974 | Roszyk et al. | 320/2 |
| 3,885,211 | 5/1975 | Gutai | 320/2 |
| 3,938,018 | 2/1976 | Dahl | 320/2 |
| 3,939,391 | 2/1976 | Winnacker | 320/2 |
| 4,030,058 | 6/1977 | Riffe et al. . | |
| 4,038,625 | 7/1977 | Tompkins et al. . | |
| 4,146,857 | 3/1979 | Schleupen . | |
| 4,260,943 | 4/1981 | Zaderej et al. | 320/21 |
| 4,303,902 | 12/1981 | Lesster et al. . | |
| 4,496,896 | 1/1985 | Melocik et al. | 320/2 |
| 4,543,556 | 9/1985 | Taylor et al. . | |
| 4,654,573 | 3/1987 | Rough et al. | 320/2 |
| 4,800,328 | 1/1989 | Bolger et al. | 320/2 |
| 4,827,550 | 5/1989 | Graham et al. . | |

(List continued on next page.)

FOREIGN PATENT DOCUMENTS 40-6105471  4/1994  Japan ........................... 336/DIG. 2

OTHER PUBLICATIONS

"Electromagnetic Fields," Consumer Reports, May 1994, pp. 354–359.
"Exposure to Residential Electric and Magnetic Fields and Risk of Childhood Leukemia," University of Southern California, Electric Power Research Institute EN–7464, Project 2964–1, Interim Report (Report Summary only), Nov. 1991.
"Exploring the Options for Magnetic Field Management," EPRI Journal, Oct./Nov. 1990, pp. 5–19.
Gordon Miller, "Exposure Guidlines for Magnetic Fields," American Industrial Hygiene Association Journal, Dec. 1987, vol. 48, pp. 957–968.
J. R. Gauger, "Household Appliance Magnetic Field Survey," IEEE Transactions on Power Apparatus and Systems, Sep. 1985, vol. PAS–104, No. 9.

*Primary Examiner*—Edward Tso
*Attorney, Agent, or Firm*—Haverstock & Associates

[57] ABSTRACT

An improved system for charging a battery of a hand held device, such as an electric toothbrush. The system has a first coil coupled around a first magnetic core. The first magnetic core forms a substantially closed magnetic path except for a core gap. An AC power signal is applied to the first coil to create a varying magnetic field within the core gap. The core gap is configured to minimize radiation of magnetic flux whether the second magnetic core is in place or not by having its faces closely spaced and aligned substantially parallel to one another. A second coil is coupled around a second magnetic core. The second magnetic core is insertable into the core gap to form an AC current in the second coil. The second magnetic core is sized to substantially occupy the core gap to minimize radiation of magnetic flux. The size of the gap and the length of the second magnetic core are made as small as possible to keep the weight of the hand-held device low. The second coil is coupled to a rectifier which is in turn coupled to charge the battery.

15 Claims, 6 Drawing Sheets

U.S. PATENT DOCUMENTS

| | | |
|---|---|---|
| 4,827,551 | 5/1989 | Maser et al. . |
| 4,827,552 | 5/1989 | Bojar et al. . |
| 4,845,795 | 7/1989 | Crawford et al. . |
| 4,845,796 | 7/1989 | Mosley . |
| 4,912,391 | 3/1990 | Meadows ................................ 320/2 |
| 4,942,352 | 7/1990 | Sano ............................................ 320/2 |
| 5,070,293 | 12/1991 | Ishii et al. ................................... 320/2 |
| 5,157,319 | 10/1992 | Klontz et al. .............................. 320/2 |
| 5,216,402 | 6/1993 | Carosa . |
| 5,264,776 | 11/1993 | Hulsey ........................................ 320/2 |
| 5,367,242 | 11/1994 | Hulman ...................................... 320/2 |

CHARGER FOR HAND-HELD RECHARGEABLE ELECTRIC APPARATUS WITH REDUCED MAGNETIC FIELD

This is a Continuation-In-Part of application Ser. No. 08/269,392, which was filed on Jun. 30, 1994, which has been abandoned.

FIELD OF THE INVENTION

This invention relates to electrically-operated hand-held devices. More specifically, it relates to hand-held devices operated by rechargeable batteries in which the recharger is coupled to the hand-held device through a mechanically separable transformer.

BACKGROUND

Hand-held battery-operated devices are well known in the art. Oral hygiene devices in this category, such as electric toothbrushes, are also well know in the art.

Battery operation is both more convenient and safer than operating from standard alternating current (AC) outlets. Devices equipped with rechargeable batteries are even more convenient, because the batteries do not have to be replaced periodically.

One well known technique for recharging such batteries is to equip the hand-held device with an electrical connector. A recharger, which typically converts the high voltage AC available from an outlet to low voltage AC or direct current (DC), is coupled electrically to this connector. Devices that employ this approach are disclosed in U.S. Pat. Nos. 4,827,551 and 4,827,552. This technique has two well-known disadvantages. First, it requires a hole for the connector through the device's enclosure, making it difficult to seal the device's internal parts against water, dirt, solvents, and so forth. Second, it provides an unlikely but still possible electrical connection between the user of the hand-held device and the AC outlet.

An improved charger, known in the art, eliminates any electrical connection between the hand-held device and the AC outlet. Instead, the required recharging power is coupled magnetically between the recharger and the hand-held device. The charger contains the primary of a transformer, and the hand-held device contains the secondary of a transformer. The primary and the secondary of the transformer are mechanically separable. When the two are placed in proper orientation and close proximity and the primary is electrically coupled to an AC outlet, a varying magnetic field is electrically induced in the primary of the transformer, and is then coupled to the secondary of the transformer. The secondary coil of the transformer is used to generate charging current for the rechargeable batteries. This approach allows the hand-held device to be completely sealed, and provides no electrical connection between an AC outlet and the hand-held device.

One device that employs such a charging arrangement is the Interplak® Home Plaque Removal Instrument manufactured by Bausch & Lomb of Tucker, Ga., and described, in part, in the disclosure of U.S. Pat. No. 4,845,795. However, such an approach can produce substantial low- and medium-frequency magnetic fields in the vicinity of the charger.

Although at present there are no widely-accepted limits on human exposure to magnetic fields, most authorities recommend prudent avoidance. Many authorities especially recommend avoiding exposing children to magnetic fields for lengthy periods of time.

Chargers for electric toothbrushes of the type described above are often intended to operate continuously. For example, the charger for the Interplak® does not have an on/off switch; it is simply plugged into an outlet. Such chargers are often placed in bathrooms, and bathrooms are often adjacent to rooms in which children sleep. Common building materials such as wood, drywall, and plaster have no effect on the propagation of magnetic fields. Consequently, it is possible for children to be inadvertently and unknowingly exposed, for lengthy periods of time while they sleep, to magnetic fields emanating from such prior-art chargers.

Turning to FIG. 1, we see a prior-art electric toothbrush 2 resting in a recess in its prior-art charger/base 1. The charger/base is connected to a power source such as an AC outlet through a cable 6. Through a portion of the charger/base that has been cut away, we see a primary transformer winding 7, which may be driven directly with the AC current delivered through the cable 6. Alternatively, the primary transformer winding 7 may be driven with a higher frequency current generated by an electronic circuit contained somewhere within the charger/base 1, which in turn receives power from the cable 6.

Examining the prior-art electric toothbrush 2 of FIG. 1, we see that it incorporates an on/off switch 4. A mechanical activator, such as a motor, inside the toothbrush 2 drives a shaft through the neck 5 of the toothbrush, which in turn activates the head of the toothbrush.

The head of the toothbrush may be of any type such as those disclosed in U.S. Pat. Nos. 4,827,550, 4,827,551, 4,827,552, or 4,845,796, and is not shown in FIG. 1 or FIG. 2 because the form of the head is not relevant to the present invention.

Inspecting the lower end of the toothbrush 2 in FIG. 1, we see that it rests in a recess formed in the charger/base 1. We see that a portion of the toothbrush 2 has been cut away, revealing the bottom end of a rechargeable battery 3, a rectifier 9, and a transformer secondary coil 9. The transformer secondary coil 9 converts a portion of the varying magnetic field, which was formed by a primary alternating current flowing through the transformer primary coil 7, into a secondary alternating current. This secondary alternating current is rectified by the rectifier 9, then is used to recharge the battery 3 contained within the toothbrush 2.

Turning now to FIG. 3A, we see the prior art transformer primary coil 7 and transformer secondary coil 8 of FIG. 1 more clearly. FIG. 3A, for clarity, has omitted all of the charger/base 1 and toothbrush 2 of FIG. 1.

It will be apparent to one familiar with the art that the prior-art form of transformer shown in FIG. 3A forms a substantially open magnetic circuit, and that lines of magnetic flux will radiate outwards from this transformer in an essentially toroidal form.

Turning now to FIG. 3B, we see a prior art separable transformer that forms a substantially closed magnetic circuit, thus reducing the radiation of lines of magnetic flux under most circumstances. A primary core 34, surrounded by a primary winding 33, is magnetically coupled to a separable secondary core 31 and its associated secondary winding 32. It will be apparent to one familiar with the art that this prior art has an important disadvantage if radiated magnetic fields are a concern. When the separable secondary core 32 is separated from the primary core 34, the primary will form an essentially open magnetic circuit and that magnetic lines of flux will radiate from the primary faces 35. It will also be apparent to one familiar with the art that such a pot-core can be of practical use only at frequencies substantially higher than power-line frequencies. Prior art of this type may be found in the disclosures of U.S. Pat. Nos. 2,967,267, 3,292,579, 3,840,795 (FIGS. 7 and 8), 4,038,625, 4,942,352, and 5,157,319.

Turning now to FIG. 3C, we see a prior art separable transformer, with a magnetically permeable core 43 placed coaxially between a primary coil 41 and a secondary coil 42. It will be apparent to one familiar with the art that this prior art has an important disadvantage if radiated magnetic fields are a concern, because the core does not form a closed magnetic circuit and therefore allows lines a magnetic flux to radiate outwards from the primary coil in a toroidal form stretched along the axis of the core 43. Such prior art separable transformers may be found in the disclosures of U.S. Pat. Nos. 3,418,552 and 3,840,795 (FIG. 9), and may be found in the Oral-B Plaque Remover™ electric toothbrush manufactured by Braun, Inc. of Lynnfield, Mass.

Turning now to FIG. 3D, we see a prior art separable transformer that forms a substantially closed magnetic circuit, thus reducing the radiation of lines of magnetic flux under most circumstances. A primary core 53, surrounded by a primary winding 51, is magnetically coupled to a separable secondary core 54 and its associated secondary winding 52. It will be apparent to one familiar with the art that this prior art has an important disadvantage if radiated magnetic fields are a concern. When the separable secondary core 54 is separated from the primary core 53, the primary will form an essentially open magnetic circuit and that magnetic lines of flux will radiate from the primary faces 55. It will also be apparent to one familiar with the art that such a secondary core 54 may contribute substantial weight to a hand-held device. Such added weight can make a hand-held device such as a toothbrush cumbersome and/or perhaps impossible to use for the time period necessary for tooth brushing for small children, the elderly or the infirm. Prior art of this type may be found in the disclosures of U.S. Pat. Nos. 3,277,358, 3,549,990, 3,772,625, 4,030,058, and 4,912,391.

Turning now to FIG. 3E, we see a prior art separable transformer that forms a substantially closed magnetic circuit, thus reducing the radiation of lines of magnetic flux under most circumstances. A primary core 63, surrounded by a primary winding 61, is magnetically coupled to a separable secondary core 64 and its associated secondary winding 62. It will be apparent to one familiar with the art that this prior art has an important disadvantage if radiated magnetic fields are a concern. When the separable secondary core 64 is separated from the primary core 63, the primary will form an essentially open magnetic circuit and that magnetic lines of flux will radiate from the primary faces 65. It will also be apparent to one familiar with the art that such a secondary core 64 may contribute substantial weight to a hand-held device. Prior art of this type may be found in the disclosures of U.S. Pat. Nos. 3,938,018 and 4,146,857.

Turning now to FIG. 3F, we see a prior art separable transformer that forms a substantially closed magnetic circuit, thus reducing the radiation of lines of magnetic flux under most circumstances. A primary core 73, surrounded by a primary winding 71, is magnetically coupled to a separable secondary core 74 and its associated secondary winding 72. It will be apparent to one familiar with the art that this prior art has an important disadvantage if radiated magnetic fields are a concern. When the separable secondary core 74 is separated from the primary core 73, the primary will form an essentially open magnetic circuit and that magnetic lines of flux will radiate from the primary faces 75. It will also be apparent to one familiar with the art that such a secondary core 74 may contribute substantial weight to a hand-held device. Prior art of this type may be found in the disclosures of U.S. Pat. Nos. 2,415,688 and 3,641,336.

It is desirable to minimize the weight of the secondary portion of a mechanically separable transformer, which is found in the hand-held portion of the device, in order to minimize hand strain and encourage proper operation of the hand-held device.

It is desirable to minimize the radiated magnetic field emitted by the charger base when the hand-held device is removed from the charger.

It is an object of the present invention to retain the advantages of a mechanically-separable transformer charger arrangement for hand-held rechargeable-battery operated devices, while substantially reducing the strength of the low- and medium-frequency magnetic fields produced near such a charger arrangement.

It is a further object of the present invention to minimize the weight of the transformer secondary in such a reduced-field implementation.

It is a further object of the present invention to minimize the magnetic flux emitted by the charger base when the hand-held device is removed from the base.

SUMMARY OF THE INVENTION

The invention is an improved system for charging a battery of a hand held device, such as an electric toothbrush. The system has a first coil coupled around a first magnetic core. The first magnetic core forms a substantially closed magnetic path except for a core gap. An AC power signal is applied to the first coil to create a varying magnetic field within the core gap. The core gap is configured to minimize radiation of magnetic flux. A second coil is coupled around a second magnetic core. The second magnetic core is insertable into the core gap to form an AC current in the second coil. The second magnetic core is sized to substantially occupy the core gap to minimize radiation of magnetic flux. The second coil is coupled to a rectifier which is in turn coupled to charge the battery.

DETAILED DESCRIPTION OF THE PREFERRED EMBODIMENT

Figure 1:
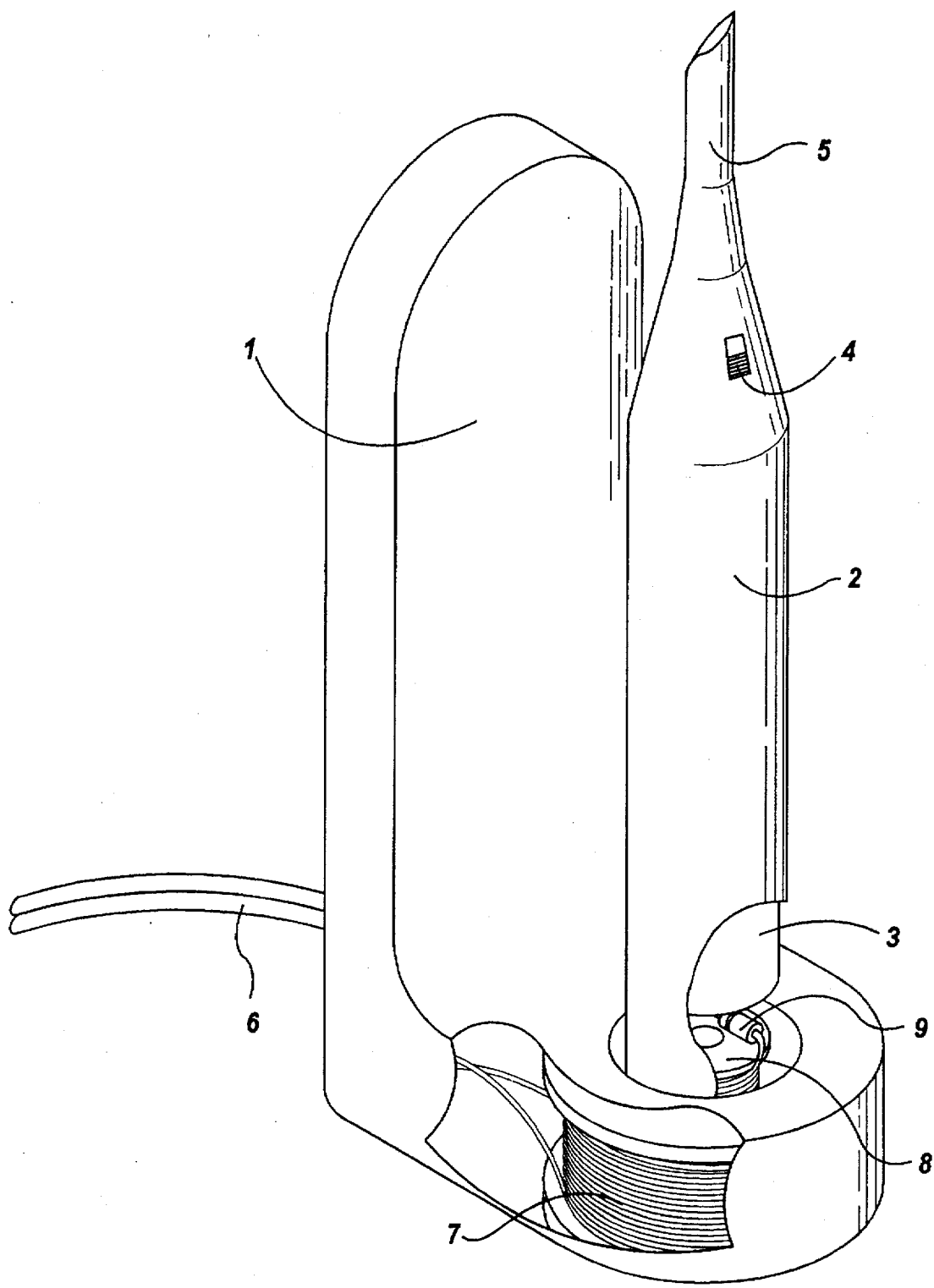
FIG. 1 is a perspective view of a prior-art electric toothbrush, placed in its recharger/holder, with portions of the toothbrush and its recharger/holder cut away to reveal the prior-art mechanically separable transformer.
Figure 2:
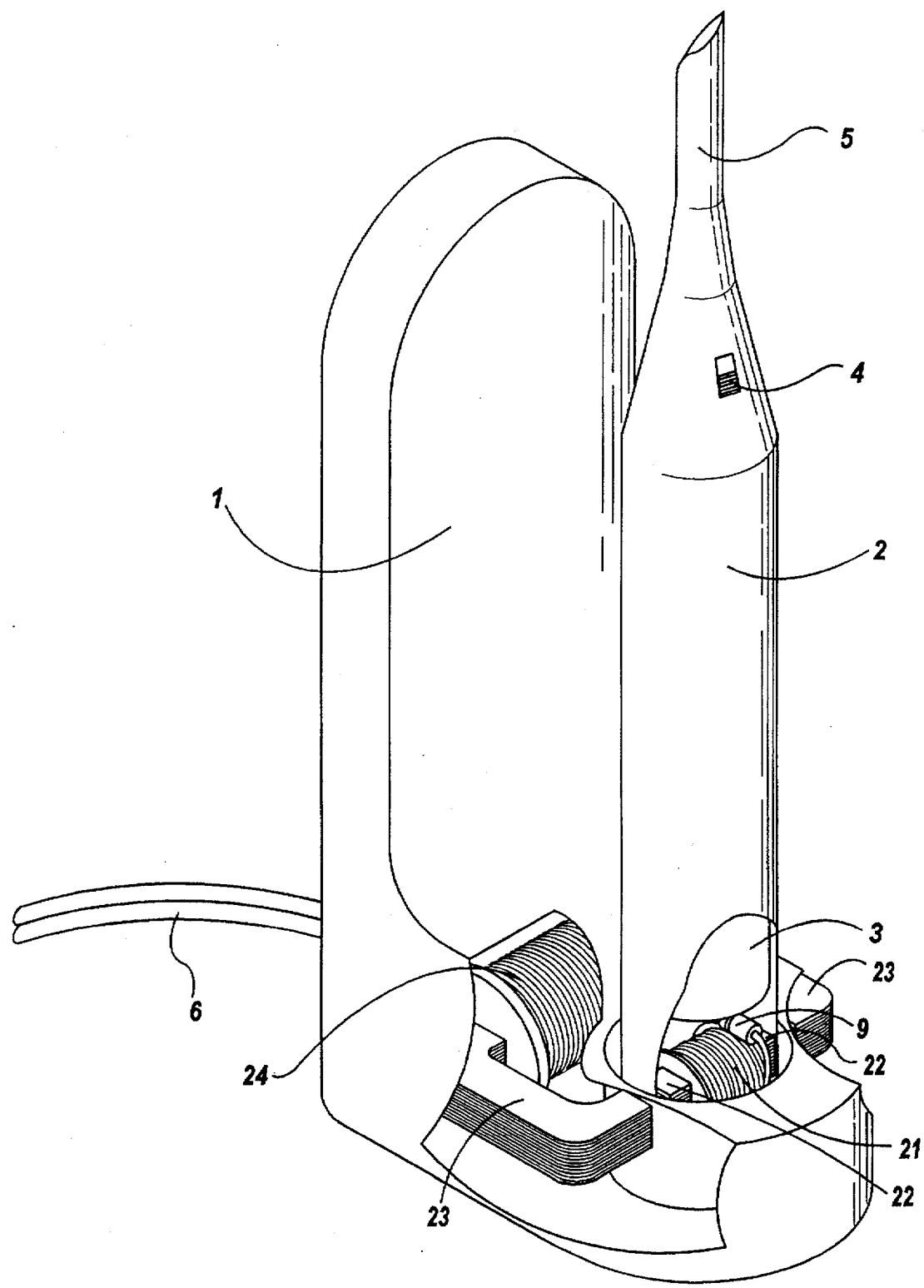
FIG. 2 is a perspective view of the present invention, as applied to the prior-art electric toothbrush of FIG. 1, again with portions of the toothbrush and its recharger/holder cut away to reveal the mechanically separable transformer of the present invention.

Turning to FIG. 2, we see an embodiment of the present invention, drawn in such a way as to conveniently contrast with the prior art of FIG. 1. The charger/base 1 and toothbrush 2 are substantially the same as in FIG. 1, but the separable transformer 7, 8 of FIG. 1 has been replaced by a separable transformer of a different magnetic design. This new transformer consists of a primary winding 24 encircling a 'C'-shaped core 23, and a secondary winding 21 encircling a short, straight section of core 22. The short, straight section of core 22 is positioned so that it substantially fills the gap in the 'C'-shaped core 23. The primary winding 24 and its associated 'C'-shaped core 23 are contained within the charger/base 1, and the secondary winding 21 and its associated core 22 are contained within the toothbrush 2.

Figure 4A:
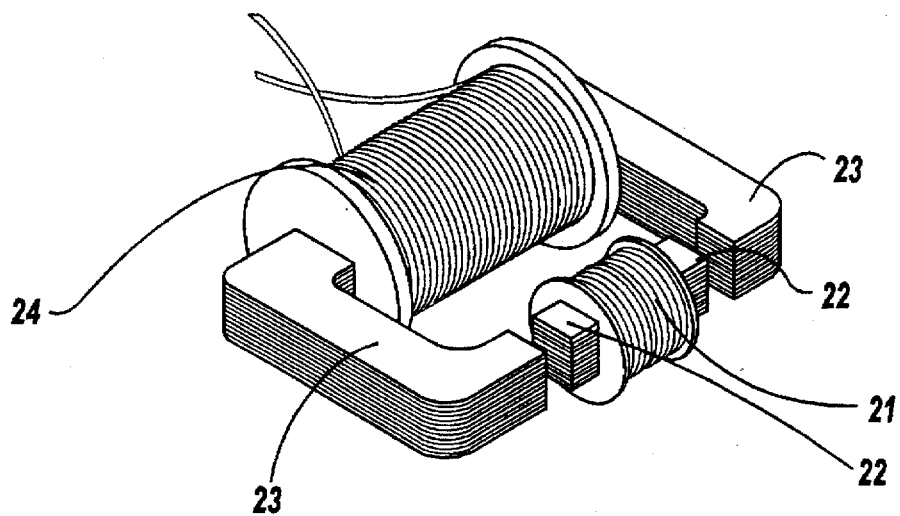
FIG. 4A is a perspective view of an embodiment of the separable transformer of the present invention, drawn in such a way as to conveniently contrast with the prior art shown in FIG. 3A, and shown removed from the prior-art toothbrush and recharger/holder of FIG. 2 for increased clarity.

Turning now to FIG. 4A, we see the transformer primary coil 24, its associated 'C'-shaped core 23, the secondary winding 21 and its associated core 22 of FIG. 2 more clearly. FIG. 4A for clarity has omitted all of the charger/base 1 and toothbrush 2 of FIG. 2.

It will be apparent to one familiar with the art that the core 23, 22 of the transformer shown in FIG. 4A forms a substantially closed magnetic circuit, and consequently confines the magnetic lines of flux to the path of the core 22, 23. A minor amount of magnetic flux radiates outwards from the gaps between cores 22 and 23.

Figure 3A:
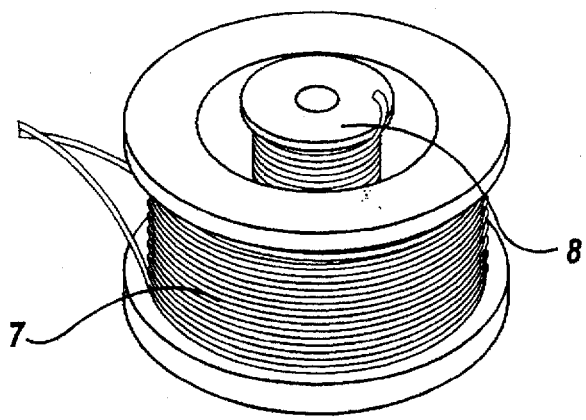
FIG. 3A is a perspective view of a prior-art separable transformer, shown removed from the prior-art toothbrush and recharger/holder of FIG. 1 for increased clarity.
Figure 3B:
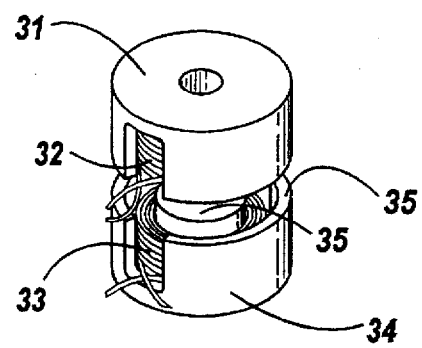
FIG. 3B is a perspective view of another prior-art separable transformer, commonly referred to as a pot core transformer.
Figure 3C:
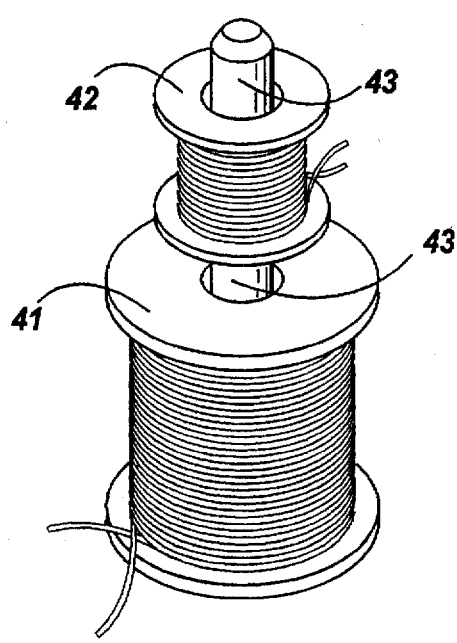
FIG. 3C is a perspective view of yet another prior-art separable transformer, commonly referred to as a co-axial core transformer.

I have determined by experiment that the magnetic field strength at a given distance for a transformer of the form shown in FIG. 3B, when compared with an otherwise identical transformer of the prior-art form shown in FIG. 3A operating under otherwise identical conditions, is lower by more than two orders of magnitude.

The cores 22, 23 may be formed of any convenient ferromagnetic material, such as grain-oriented silicon steel or ferrite.

It will be apparent to one familiar with the art that the physical alignment of the secondary core 22 of FIG. 4A within the gap in the primary core 23 is moderately critical in that the secondary core 22 should substantially span the gap in the primary core 23. This alignment may be accomplished with any convenient mechanical means, such as forming a tab in the bottom of the toothbrush 2 of FIG. 2 which mates with a corresponding slot in the charger/base 1, or by forming the handle of the toothbrush 2 into an oval cross section and forming the recess in the charger/base 1 into a corresponding oval cross section.

Figure 3D:
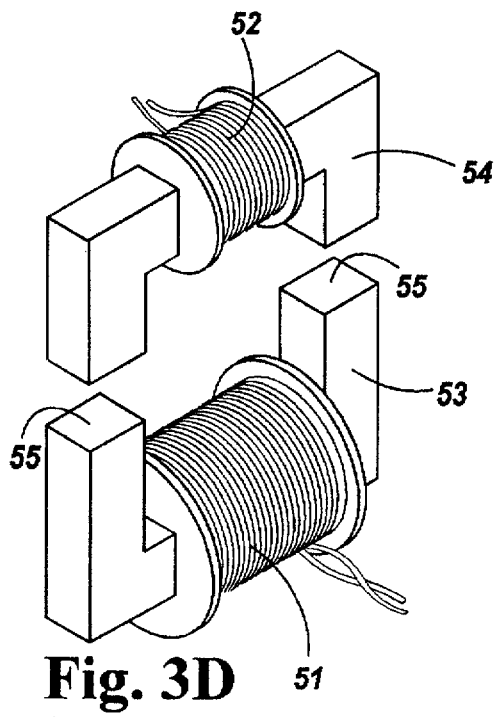
FIG. 3D is a perspective view of yet another prior-art separable transformer, commonly referred to as a 'U' core transformer.
Figure 3E:
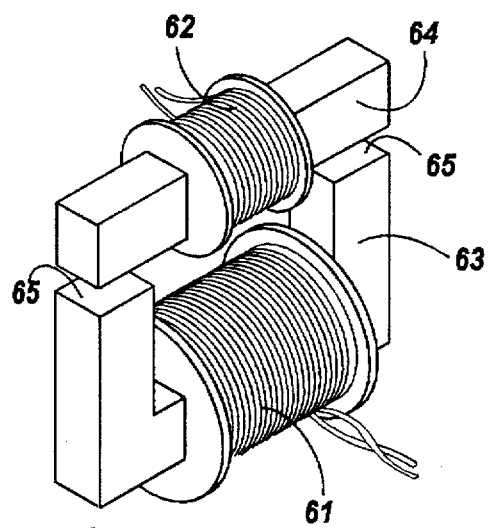
FIG. 3E is a perspective view of yet another prior-art separable transformer, also commonly referred to as a 'U' core transformer.
Figure 3F:
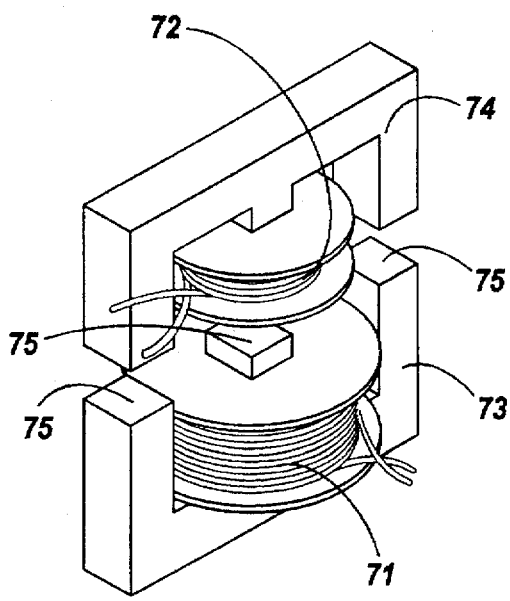
FIG. 3F is a perspective view of yet another prior-art separable transformer, commonly referred to as an 'E' core transformer.
Figure 4B:
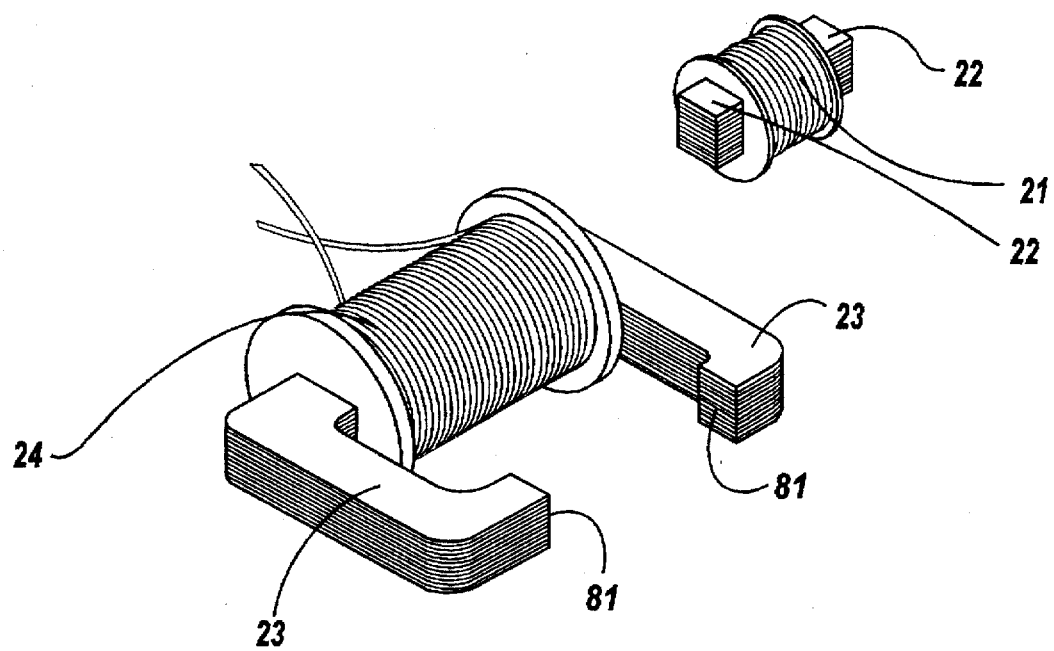
FIG. 4B is a perspective view of an embodiment of the separable transformer of the present invention, with the secondary moved a little distance to more clearly reveal a key element of the present invention.

Turning now to FIG. 4B, we see the separable transformer of FIG. 4A operating with the its secondary 21, 22 in its separated position, as it would be, for example, when a toothbrush is being used rather than when it is resting in its charging base. It will be apparent to one familiar with the art that lines of magnetic flux will travel directly between primary faces 81, but will balloon outward somewhat in the center of the gap defined by primary faces 81. This provides a marked improvement over the prior art embodiments shown for example in FIGS. 3D, 3E and 3F.

Figure 5:
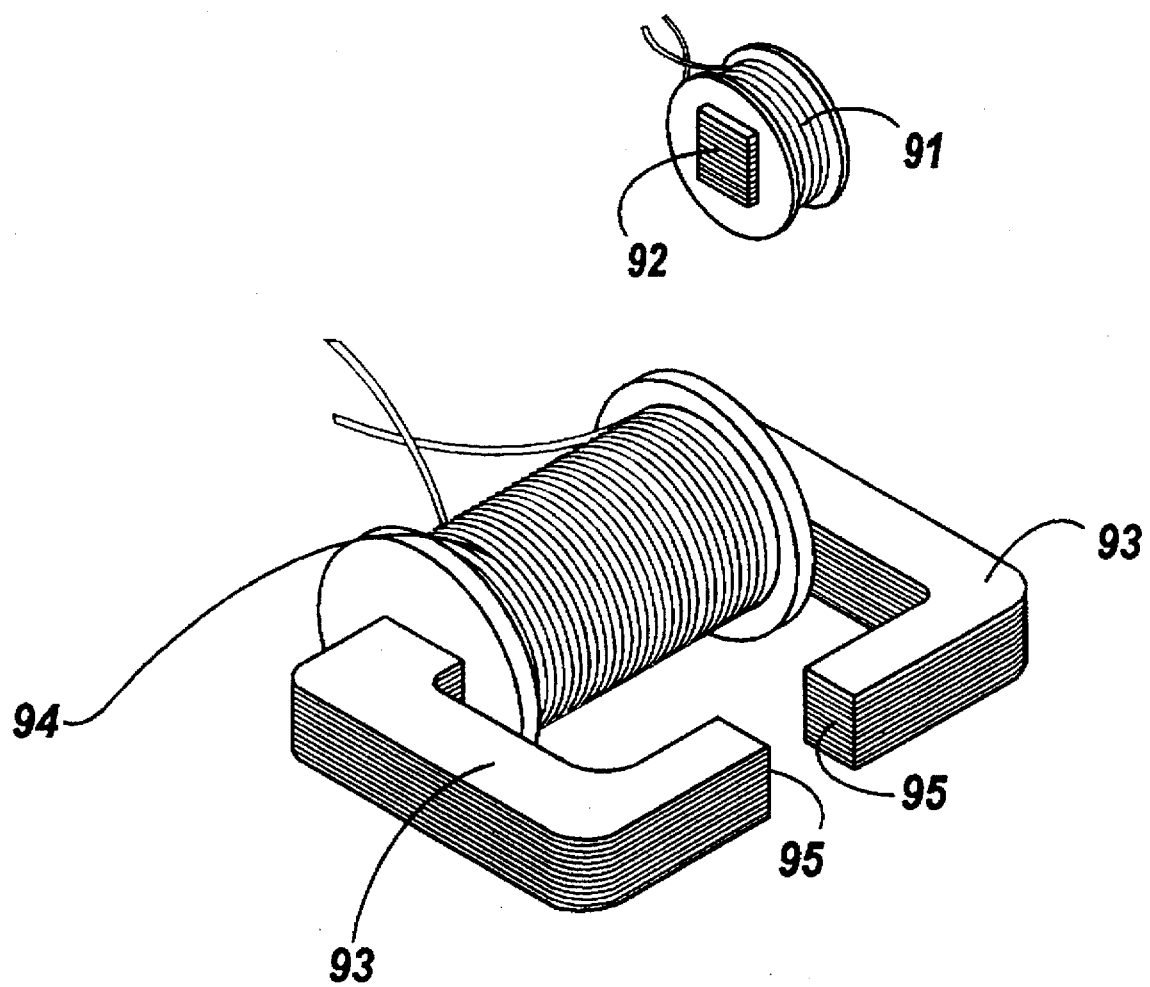
FIG. 5 is a perspective view of the preferred embodiment of the separable transformer of the present invention.

It should be apparent that the embodiment of the present invention shown in FIGS. 4A and 4B contrasts conveniently with the prior art of FIGS. 1 and 3A, but that the advantages of the present invention can best be seen in the embodiment show in FIG. 5.

Turning now to FIG. 5, we see the preferred embodiment of the present invention. A separable transformer is formed of a primary coil 94, primary core 93, secondary coil 91, and secondary core 92. The primary core 93 and secondary core 92 together form a closed magnetic path, thus minimizing the radiation of magnetic lines of flux. The weight of the secondary 91, 92 is minimized by keeping the secondary core 92 as short as practical. In the preferred embodiment, the secondary core 92 is less than ½" long. Keeping the secondary core 92 short has the additional advantage of minimizing the distance between the faces 95 of the primary core, thus minimizing the radiation of magnetic flux when the secondary 91, 92 is separated for use. The primary core 93 and the secondary core 92 may be formed of any low reluctance material, such as laminated grain-oriented silicon steel.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention. Specifically, it will be apparent that to one of ordinary skill in the art that the device of the present invention could be implemented in several different ways and the apparatus disclosed above is only illustrative of the preferred embodiment of the invention and is in no way a limitation.

What is claimed is:

1. A system including a first electric circuit for transferring AC electric power to a second electric circuit which is mounted within a portable hand-held device such that the second electric circuit and the device are separable from the first electric circuit, wherein there is no electrical connection between the first electric circuit and the second electric circuit, wherein the first electric circuit comprises a first coil coupled around a first magnetic core such that the first coil is coupled to receive an AC power signal for forming a varying magnetic field, and wherein the second circuit comprises a second magnetic coil coupled around a second magnetic core for receiving the varying magnetic field, the system wherein the first magnetic core forms a substantially closed magnetic path having a magnetic core gap, such magnetic core gap having a first gap face and a second gap face which are aligned to each other, and the second magnetic core fits within and is substantially aligned with the magnetic core gap at those times when the second magnetic circuit is magnetically coupled to the first magnetic circuit such that the radiation of the magnetic flux is minimized when the second magnetic core is aligned and also when separated from the first magnetic core.

2. The second circuit according to claim 1 further comprising a rectifier coupled to the coil and a battery coupled to the rectifier for storing power.

3. The second circuit according to claim 2 wherein the size of the core gap is minimized to reduce the radiation of magnetic flux and wherein the second magnetic core is sufficiently large to accommodate sufficient windings of the second coil to charge the battery.

4. The second circuit according to claim 3 wherein the core gap is substantially ½ inch.

5. The system according to claim 2 wherein the first circuit is mounted within a base unit.

6. The system according to claim 5 wherein the device comprises a portable electric toothbrush.

7. The system according to claim 5 wherein the device comprises a portable electric shaver.

8. The system according to claim 5 wherein the device comprises a portable telephone.

9. The system according to claim 5 wherein the device comprises a portable flashlight.

10. The system according to claim 5 wherein the device comprises a portable computer.

11. The system according to claim 5 wherein the device comprises a portable electric screwdriver.

12. A system for transferring electric power from a first circuit to a second circuit comprising;
   a. a first electric circuit comprising a first coil coupled around a first magnetic core wherein the first coil is coupled to receive an AC power signal for forming a varying magnetic field, wherein the first magnetic core has a core gap, and the core gap having a first gap face and a second gap face wherein the first gap face is substantially parallel to the second gap face and wherein the first gap face and the second gap face are spaced and aligned to minimize radiation of magnetic flux such that the first magnetic core forms a substantially closed magnetic path; and
   b. a second electric circuit comprising a second coil coupled around a second magnetic core for receiving the varying magnetic field wherein the second magnetic core has a first end and a second end and wherein the second magnetic core is insertable into the core gap so that the first end is aligned with the first gap face and the second end is aligned with the second gap face to more fully close the magnetic path such that the radiation of the magnetic flux is minimized when the second magnetic core is aligned and also when separated from the first magnetic core.

13. The system according to claim 12 wherein the second coil is coupled to rectifier for charging a battery coupled to the rectifier.

14. The circuit according to claim 13 wherein the size of the core gap is minimized to reduce the radiation of magnetic flux and wherein the second magnetic core is sufficiently large to accommodate sufficient windings of the second coil to charge the battery.

15. The second circuit according to claim 14 wherein the core gap is substantially ½ inch.

\* \* \* \* \*